United States Patent
Lapointe et al.

(10) Patent No.: US 12,259,327 B2
(45) Date of Patent: Mar. 25, 2025

(54) SYSTEM AND METHOD FOR PERFORMING A PHOTOLUMINESCENCE ANALYSIS ON A MEDIUM

(71) Applicant: ZILIA INC., Quebec (CA)

(72) Inventors: Nicolas Lapointe, Québec (CA);
Damon Depaoli, Québec (CA);
Dominic Sauvageau, Québec (CA)

(73) Assignee: ZILIA INC., Quebec (CA)

( * ) Notice: Subject to any disclaimer, the term of this patent is extended or adjusted under 35 U.S.C. 154(b) by 636 days.

(21) Appl. No.: 17/616,786

(22) PCT Filed: Jun. 5, 2020

(86) PCT No.: PCT/CA2020/050778
§ 371 (c)(1),
(2) Date: Dec. 6, 2021

(87) PCT Pub. No.: WO2020/243842
PCT Pub. Date: Dec. 10, 2020

(65) Prior Publication Data
US 2022/0307983 A1    Sep. 29, 2022

Related U.S. Application Data

(60) Provisional application No. 62/857,345, filed on Jun. 5, 2019.

(51) Int. Cl.
*G01N 21/64*    (2006.01)
*A61B 3/12*    (2006.01)
(Continued)

(52) U.S. Cl.
CPC .......... *G01N 21/6456* (2013.01); *A61B 3/12* (2013.01); *A61B 3/14* (2013.01); *A61B 5/0071* (2013.01);
(Continued)

(58) Field of Classification Search
CPC .......... G01N 21/6456; G01N 21/6486; G01N 21/65; G01N 2021/6421; G01N 2021/653;
(Continued)

(56) References Cited

U.S. PATENT DOCUMENTS 6,822,741 B2 * 11/2004 Aronkyto .............. G01J 3/0275
356/417
2007/0177149 A1    8/2007 Aronkyto et al.
2017/0017069 A1    1/2017 Siegel et al.

FOREIGN PATENT DOCUMENTS

CN    103163111 A    6/2013
CN    109477795 A    3/2019
(Continued)

OTHER PUBLICATIONS

International Search Report and Written Opinion from PCT Application No. PCT/CA2020/050778, Jul. 17, 2020.
(Continued)

*Primary Examiner* — James C. Jones
(74) *Attorney, Agent, or Firm* — Workman Nydegger

(57) ABSTRACT

Systems and methods for performing a photoluminescence analysis on a medium such as the fundus of a patient's eye are provided. An imaging device, a spectral analyser and an excitation light source are provided. An optical assembly defines an imaging light path between the patient's eye and the imaging device and a spectral analysis light path between an analysis spot on the patient's eye and the spectral analyser. The excitation light source generates an excitation light beam comprising an excitation wavelength selected to excite components present in the patient's eye for the generation of fluorescent light at a photoluminescence wavelength, and is optically coupled to the spectral analysis light path for projecting the excitation light beam on the analysis spot. An optical filter is coupled to the spectral analyser, and
(Continued)

has a low light transmissivity at the excitation wavelength and a high light transmissivity at the photoluminescence wavelength.

18 Claims, 10 Drawing Sheets

(51) Int. Cl.
    *A61B 3/14*     (2006.01)
    *A61B 5/00*     (2006.01)
    *G01N 21/65*     (2006.01)

(52) U.S. Cl.
    CPC ......... *G01N 21/6486* (2013.01); *G01N 21/65* (2013.01); *G01N 2021/6421* (2013.01); *G01N 2021/653* (2013.01)

(58) Field of Classification Search
    CPC ........... A61B 3/12; A61B 3/14; A61B 5/0071; A61B 3/0008; A61B 5/0075
    See application file for complete search history.

(56) References Cited

FOREIGN PATENT DOCUMENTS

| EP | 1138255 | A1 | 10/2001 |
|----|---------|----|---------|
| WO | 2016041062 | A1 | 3/2016 |

OTHER PUBLICATIONS

Piffaretti, "Development of Minimally-Invasive Optical Methods to Individualize the Doses Used for Therapeutic Applications of Light," Ecole Polytechnique Federale De Lausanne, Nov. 26, 2010, 187 pages.

Search Report from corresponding European Application No. 20818733.6, Jan. 17, 2023.

Chinese Office Action in corresponding Chinese Patent Appl. No. CN 202080054667.3, mailed Nov. 19, 2024, 20 pages.

\* cited by examiner

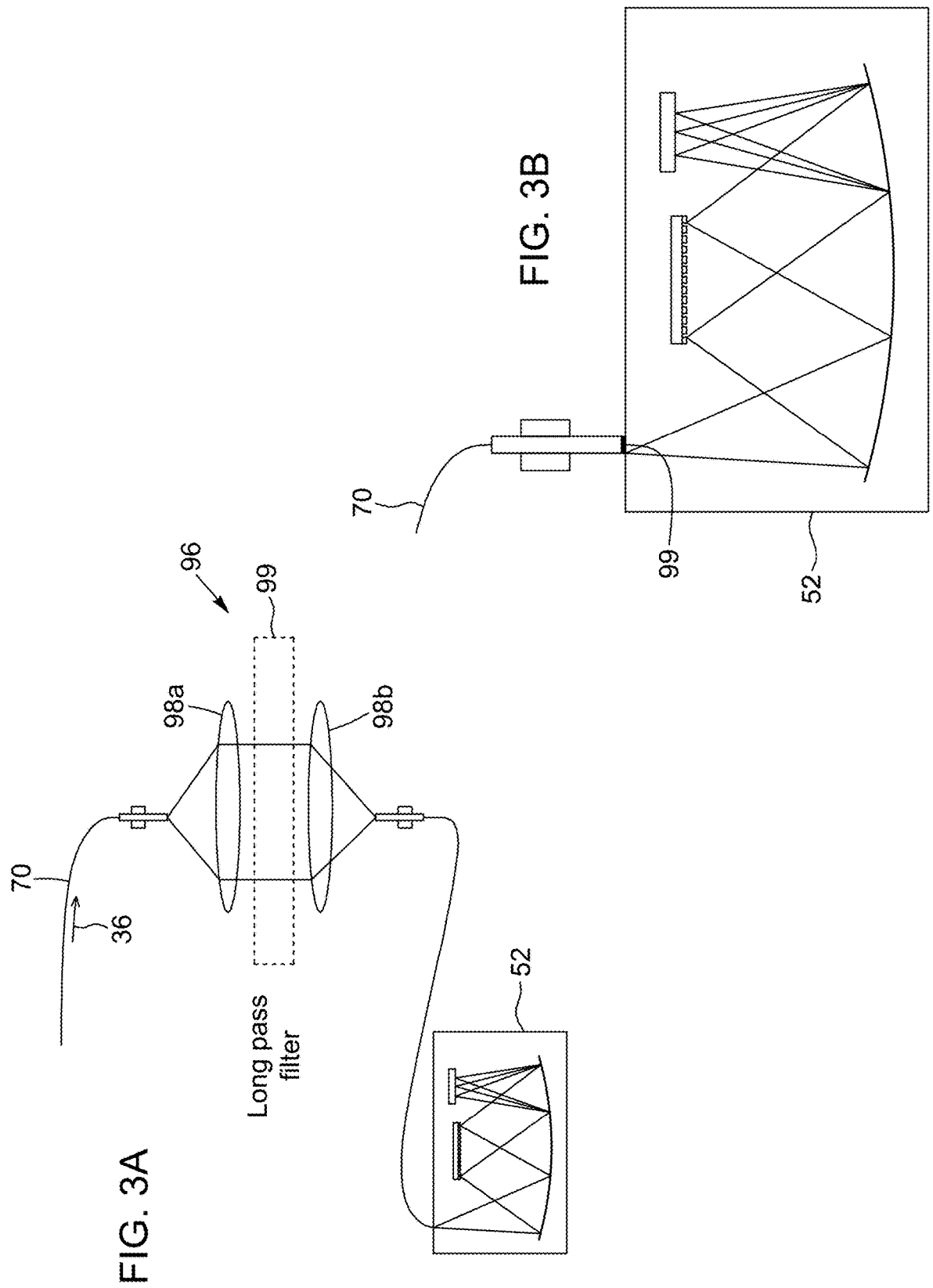

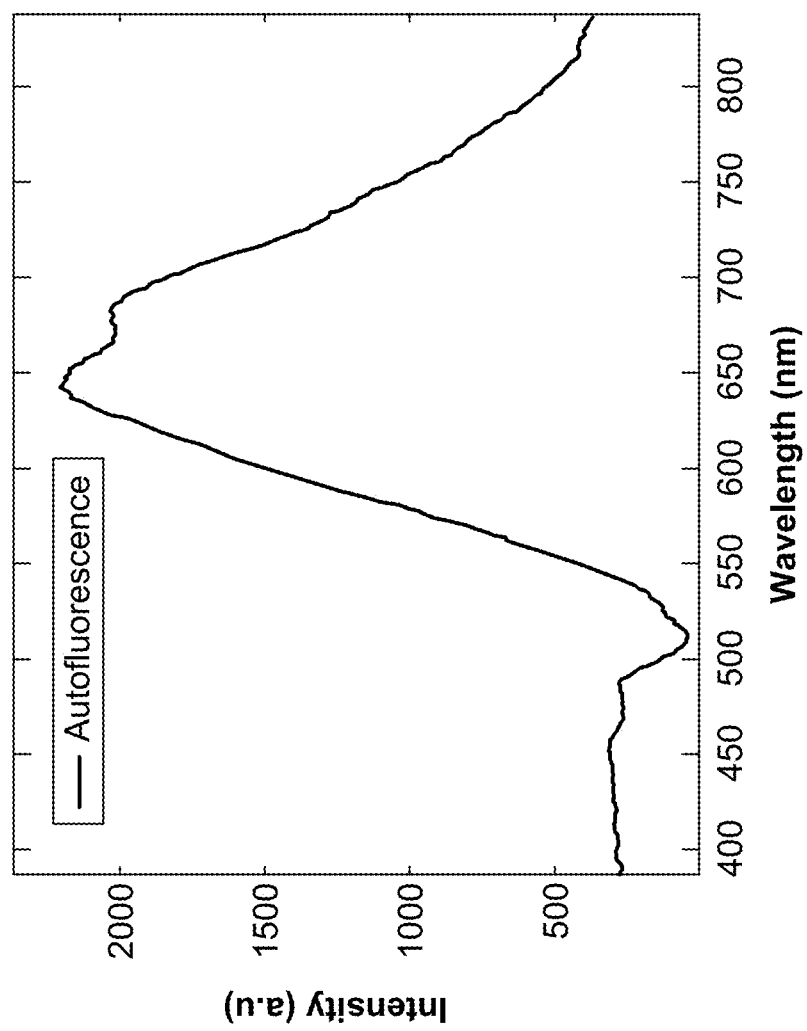
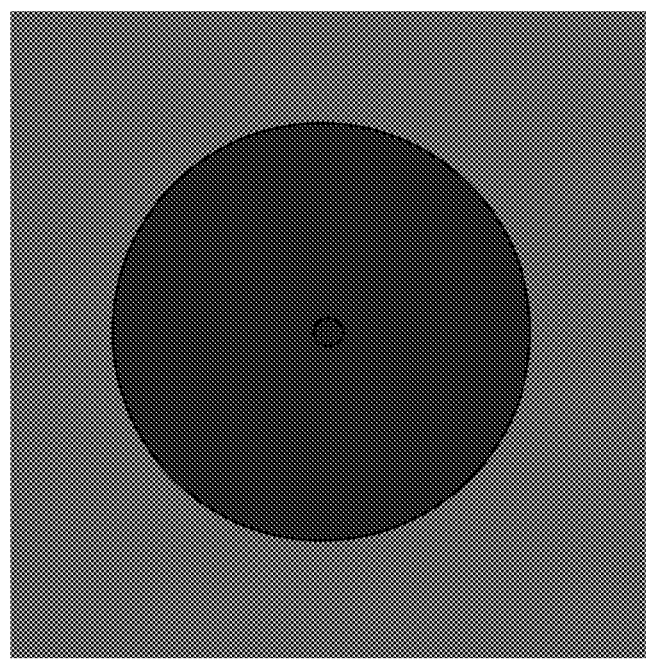
FIG. 5C
FIG. 5D

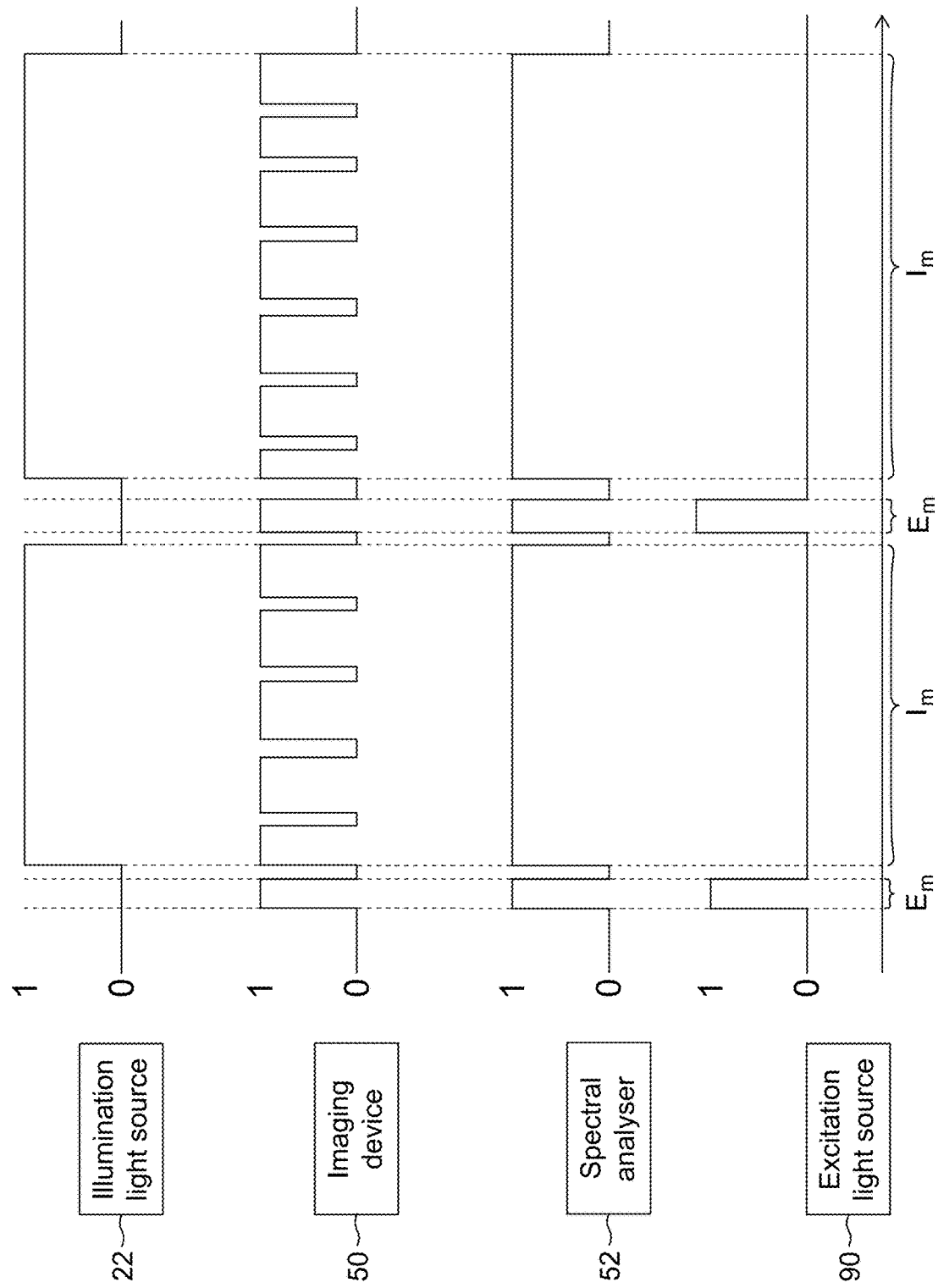

SYSTEM AND METHOD FOR PERFORMING A PHOTOLUMINESCENCE ANALYSIS ON A MEDIUM

TECHNICAL FIELD

The technical field generally relates to spectroreflectometric systems and methods and more particularly concerns devices for spectral absorbance analysis, fluorescence, autofluorescence, spontaneous Raman spectroscopy, coherent Raman spectroscopy or other eye-related measurements.

BACKGROUND

The assessment of photoluminescence of analytes (e.g. proteins or other compounds) natively present in, or photoluminescent markers added to, the retina directly or upon absorption of light at specific excitation wavelengths, is a useful non-invasive tool with widespread medical and health monitoring applications. Indeed, the assessment of photoluminescence can provide valuable information on metabolism, the pathophysiology of different illnesses and conditions, or the efficacy of administered treatments.

In addition, the combination of photoluminescence assessment with imaging provides valuable additional information on physiological and pathophysiological phenomena.

There remains a need for an improved device that can be used to quantify fluorescence, autofluorescence, spontaneous and coherent Raman spectroscopy, and perform analysis of other parameters in a patient's eye that provide at least some of the above-mentioned advantages.

SUMMARY

In accordance with one aspect, there is provided a system for performing a photoluminescence analysis on a medium.

The system includes an imaging device configured to acquire an image of the medium, including an analysis spot, a spectral analyser and an optical assembly. The optical assembly defines an imaging light path between the medium and the imaging device and a spectral analysis light path between the analysis spot on the medium and the spectral analyser.

The system further includes an excitation light source operable to generate an excitation light beam comprising an excitation wavelength selected to excite components present in the medium for the generation of photoluminescent light at an emission wavelength differing from the excitation wavelength. The excitation light source is optically coupled to the spectral analysis light path for projecting the excitation light beam on said analysis spot.

The system further includes an optical filter coupled to the spectral analyser. The optical filter has a low light transmissivity at the excitation wavelength and a high light transmissivity at the emission wavelength.

In some implementations, the system includes a beamsplitter positioned and configured to direct an imaging portion of return light from the medium travelling along the imaging light path to the imaging device and a spectral analysis portion of said return light to the spectral analysis light path. The beamsplitter may be a dichroic beamsplitter. In some variants, the beamsplitter is configured to divide the light travelling along the imaging light path into the imaging portion and the spectral analysis portion according to one of intensity ratios and polarisation directions.

In some implementations, the system includes a first optical fiber link extending between the spectral analysis light path and the spectral analyser, a second optical fiber link extending between the spectral analysis light path and the excitation light source, and a three-prong coupler optically coupling the spectral analysis light path, the first optical fiber link and the second optical fiber link. The three-prong coupler may include one of a multimode optical circulator, a double-clad optical fiber and a free-space beam-splitting configuration. In some variants, the optical filter includes a free-space optical component disposed between the first optical fiber link and the spectral analyser. In other variants, the optical filter may include a thin film deposited on a fiber-based component disposed between the first optical fiber link and the spectral analyser.

In some implementations, the optical filter is a longpass optical filter. In other implementations, the optical filter is a bandpass optical filter.

In some implementations, the system includes an illumination subassembly configured to project illumination light towards the medium. The system may further include an illumination light source operable to generate the illumination light and optically coupled to the illumination subassembly.

A controller generating control signals for controlling the illumination light source, the imaging device, the spectral analyser and the excitation light source may also be provided. The controller is preferably configured to operate in:
 an illumination mode wherein the controller turns on at least the illumination device and the imaging device; and
 an excitation mode wherein the controller turns on alt least the excitation light source and the spectral analyser.

In some implementations, the system includes a controller configured to operate in:
 an illumination mode wherein the controller operates the illumination device to project said illumination light towards the medium, the imaging device to obtain an image of the medium and the spectral analyser to obtain a spectral analysis of the analysis spot on medium; and
 an excitation mode wherein the controller operates the excitation light source to project the excitation light beam on said analysis spot and the spectral analyser to obtain a photoluminescence analysis of the analysis spot on said medium.

In some implementations, the system further includes a spot shifting mechanism positioned in the spectral analysis light path and configured to shift a position of the analysis spot over said medium.

In accordance with another aspect, there is provided a system for performing a photoluminescence analysis on the fundus of a patient's eye. The system includes:
 an imaging device configured to acquire an image of the fundus;
 a spectral analyser;
 an optical assembly defining an imaging light path between the patient's eye and the imaging device and a spectral analysis light path between an analysis spot on the patient's eye and the spectral analyser;
 an excitation light source operable to generate an excitation light beam comprising an excitation wavelength selected to excite components present in the patient's eye for the generation of photoluminescent light at a photoluminescence wavelength, the excitation light source being optically coupled to the spectral analysis light path for projecting the excitation light beam on said analysis spot; and an optical filter coupled to the spectral analyser, the optical filter having a low light transmissivity at the excitation wavelength and a high light transmissivity at the photoluminescence wavelength.

In some implementations, the system includes a beamsplitter positioned and configured to direct an imaging portion of return light from the patient's eye travelling along the imaging light path to the imaging device and a spectral analysis portion of said return light to the spectral analysis light path. The beamsplitter may be a dichroic beamsplitter. The beamsplitter may be configured to divide the light travelling along the imaging light path into the imaging portion and the spectral analysis portion according to one of intensity ratios and polarisation directions.

In some implementations, the system includes a first optical fiber link extending between the spectral analysis light path and the spectral analyser, a second optical fiber link extending between the spectral analysis light path and the excitation light source, and a three-prong coupler optically coupling the spectral analysis light path, the first optical fiber link and the second optical fiber link. The three-prong coupler may include one of a multimode optical circulator, a double-clad optical fiber and a free-space beam-splitting configuration.

In some implementations, the optical filter includes a free-space optical component disposed between the first optical fiber link and the spectral analyser. In other implementations, the optical filter may include a thin film deposited on a fiber-based component disposed between the first optical fiber link and the spectral analyser.

In some implementations, the optical filter may be a longpass optical filter or a bandpass optical filter.

In some implementations, the system includes an illumination subassembly configured to project illumination light towards the patient's eye. The system may further include an illumination light source operable to generate the illumination light and optically coupled to the illumination subassembly.

In some implementations. the system may include a controller generating control signals for controlling the illumination light source, the imaging device, the spectral analyser and the excitation light source. Preferably, the controller is configured to operate in:

an illumination mode wherein the controller turns on at least the illumination device and the imaging device; and an excitation mode wherein the controller turns on alt least the excitation light source and the spectral analyser.

In some implementations, the system may further include a controller configured to operate in:

an illumination mode wherein the controller operates the illumination device to project said illumination light towards the patient's eye, the imaging device to obtain an image of the fundus and the spectral analyser to obtain a spectral analysis of the analysis spot on the fundus; and an excitation mode wherein the controller operates the excitation light source to project the excitation light beam on said analysis spot and the spectral analyser to obtain a photoluminescence measurement of the analysis spot on said fundus.

In some implementations, the system further includes a spot shifting mechanism positioned in the spectral analysis light path and configured to shift a position of the analysis spot over said fundus.

In accordance with another aspect, there is provided the use of a system as above to perform a photoluminescence analysis on the fundus of a patient's eye.

In some implementations, the photoluminescence analysis includes one of as absorbance measurements, fluorescence measurements, autofluorescence measurements, spontaneous Raman spectroscopy and coherent Raman spectroscopy.

In accordance with yet another aspect, there is provided a method for performing a photoluminescence analysis on a medium. The method includes:

providing an imaging device, a spectral analyser, an optical assembly defining an imaging light path between the medium and the imaging device and a spectral analysis light path between an analysis spot on the medium and the spectral analyser, an excitation light source optically coupled to the spectral analysis path and operable to generate an excitation light beam comprising an excitation wavelength selected to excite components present in the medium for the generation of photoluminescent light at an emission wavelength differing from the excitation wavelength, and an optical filter coupled to the spectral analyser, the optical filter having a low light transmissivity at the excitation wavelength and a high light transmissivity at the emission wavelength, and an illumination light source;

operating the illumination light source to project illumination light towards the medium, and operating the imaging device to obtain an image of the medium; and operating the excitation light source to project the excitation light beam on said analysis spot and the spectral analyser to obtain a photoluminescence measurement of the analysis spot on said fundus.

In some implementations, the method further includes operating the excitation light source and the imaging device to obtain an image of said analysis spot.

In some implementations, the method further includes a step of superimposing the image of the analysis spot on the image of the medium.

In some implementations, the medium is the fundus of a patient's eye.

In some implementations, the photoluminescence measurement includes one of an absorbance measurement, a fluorescence measurement, an autofluorescence measurement, a spontaneous Raman spectroscopy measurement and coherent Raman spectroscopy measurement.

Other features and advantages will be better understood upon reading of preferred embodiments with reference to the appended drawings.

BRIEF DESCRIPTION OF THE DRAWINGS

FIGS. 3A and 3B are schematic representations of variants of the optical filter of FIG. 2.

FIG. 5C shows the autofluorescence spectrum obtained at the analysis spot;

FIG. 5D shows an image of the analysis spot appearing as a dot in the field of view of the imaging device.

FIG. 6 is a timing diagram of the operation of a system according to some implementation.

DETAILED DESCRIPTION

Figure 1:
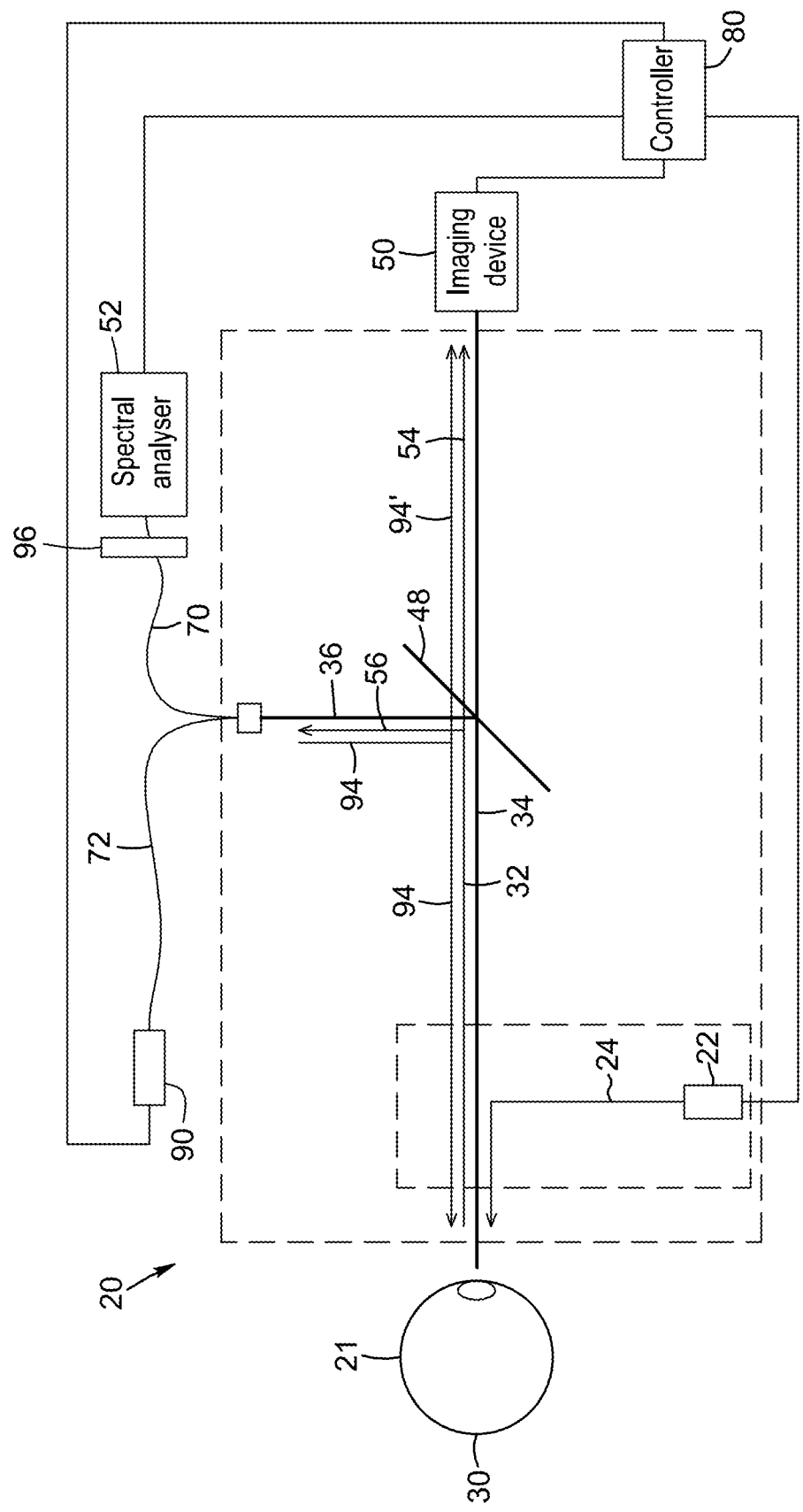
FIG. 1 is a schematic representation of a system according to an embodiment.

The present description generally relates to a system and method for performing a photoluminescence analysis of a medium such as for example an autofluorescence analysis of the fundus of a patient's eye. In some implementations, the photoluminescence analysis is combined with imaging and additional spectral analysis capabilities.

In the embodiments described herein, the system has a spectroreflectometric configuration for use in ophthalmology to study a patient's eye. In the context of the present application, the expression "spectroreflectometric" is generally used as a contraction of the terms "spectral" and "reflectometric" in reference to techniques related to spectral reflectometry. As readily understood by those skilled in the art, reflectometry refers to the use of reflected light or other electromagnetic waves to analyse the properties of a medium. Light is typically projected towards the medium and the interactions of the light wavefront with the medium leads to the returning light having optical properties affected by the medium. In spectral reflectometry, a spectral analysis of the return light, that is, an analysis of the properties of the return light as a function of its wavelength profile, is used to obtain or deduce information about the medium and its composition.

Spectral reflectometry is used for example in ophthalmologic contexts to sense oxygen levels in the fundus of the eye of a patient. By way of example, oxygen levels are assessed through the presence of oxyhemoglobin which has a characteristic light absorbance pattern. Similarly, the concentration of deoxyhemoglobin, and carboxyhemoglobin (related to the levels of carbon dioxide present) can be determined based on their respective light absorbance patterns. These compounds and their regulation are indicative of metabolism, responses to stress and stimuli and, potentially, pathophysiologies.

The expression photoluminescence generally refers to the emission of light following the absorption of photons by a medium. Optical stimulation can be caused by one or more excitation light source(s) generating light at one or more wavelengths selected to trigger the desired transitions in the medium. In the context of ophthalmology, a laser diode may for example be used to project light at an excitation wavelength on the fundus of a patient's eye. The excitation wavelength is selected to specifically interact with a known component of the eye to emit a photoluminescence light wavefront with less energy, a result of elastic interactions with the medium. This exchange of energy results in a shift in wavelength of the resulting light with respect to the excitation light, typically towards longer wavelengths. It will be readily understood that the expression photoluminescence encompasses a wide variety of techniques such as absorbance, fluorescence, autofluorescence, spontaneous and coherent Raman spectroscopies (coherent anti-Stokes Raman Scattering, stimulated Raman scattering, etc.), and the like.

In some implementations, the system and method described herein may be used to perform a fluorescence analysis of a patient's eye. The expression "fluorescence" is understood to refer to a particular type of photoluminescence resulting from a singlet-singlet electronic relaxation. In some implementations, the system and method may be used in the context of the analysis of autofluorescence from the fundus of the patient's eye. "Autofluorescence" is a special case of fluorescence where the light emission origins from molecules native to the medium under study. In other applications, the analysed fluorescence may originate from fluorophores artificially added to the medium as markers. Fluorescence imaging is a useful procedure for ophthalmological clinicians as a tool for diagnostic of various visual pathologies. By way of example, it is known to perform an autofluorescence imaging of lipofuscin granules (LGs). LGs will tend to accumulate in the retinal pigmental epithelium of the eye of patients with hereditary diseases and, in particular, in age-related macular degeneration (AMD). Quantifying the LGs at a specific location in the retina can provide better diagnoses and evaluation of the severity of diseases such as AMD. Fluorescence analysis may be performed for different regions of the fundus of the patient's eye or on other features present on the fundus. In other implementations, fluorescence analysis may be performed on other portions of the eye such as the conjunctiva.

It will be readily understood that the system and method described herein may be used for different applications than for spectroreflectometric and fluorescence analyses of the eye. More broadly, the system below may be of use in any context where spectral information from a portion of an imaged medium in response to optical excitation is desired. Various molecules and phenomena may also be studied, such as, for example, melanin fluorescence or Raman scattering, fluorescence from fluorophore markers, etc, inasmuch as they lead to alterations in the spectral profiles of return light. One skilled in the art will readily understand that in some applications the system may be used to analyze light that is either transmitted or reflected by a medium of interest. The medium under study may be other than the eye such as for example the skin, organ tissues, exposed muscle tissues, and other biological tissues or fluids. In some embodiments the medium under study may be an ex-vivo sample such as blood, tissues, etc. stored in a transparent container such as a bag, a vial, a syringe or a cuvette, or on a suitable substrate.

With reference to FIG. 1, there is shown a high-level schematized representation of a spectroreflectometric system 20 for performing a photoluminescence analysis on the fundus 30 of a patient's eye 21, in accordance with one embodiment.

The spectroreflectometric system 20 first includes an imaging device 50 and a spectral analyser 52. The spectroreflectometric system 20 further includes an optical assembly defining an imaging light path 34 between the patient's eye 21 (or other medium under study) and the imaging device 50, and a spectral analysis light path 36 between an analysis spot 82 on the patient's eye 21 and the spectral analyser 52. An illumination light source 22 controllable to generate an illumination light 24 may also be provided. The spectroreflectometric system 20 further includes an excitation light source 90 for generating an excitation light beam whose spectral contents include one or more excitation wavelengths selected to excite the generating of photoluminescent light at one or more emission wavelengths in the medium. An optical filter 96 having a low light transmissivity at the excitation wavelength or wavelengths and a high light transmissivity at the emission wavelength or wavelengths is coupled to the spectral analyser 52. The optical filter 96 is preferably a longpass filter if the emission wavelength is longer than the excitation wavelength. In some implementations where the emission wavelength is shorter than the excitation wavelength, a lowpass filter may be used. In other variants, a bandpass filter or a notch rejection filter configured to allow light at the emission wavelength through and block light at the excitation wavelength may be used.

In this illustrated configuration, the spectroreflectometric system 20 is operable in two modes: an illumination mode, and an excitation mode.

In the illumination mode, the illumination light 24 is projected towards the fundus 30 of the patient's eye 21 to illuminate it, thereby obtaining return light 32 from the fundus 30 which propagates along the imaging light path 34. Using a beamsplitter 48, the return light 32 is preferably separated into an imaging portion 54 propagating along the imaging light path 32, and a spectral analysis portion 56, diverted to the spectral analysis light path 36. The imaging portion 54 is detected via the imaging device 50 to obtain an image of the fundus 30 of the patient's eye 21.

In the excitation mode, the excitation light source 90 generates an excitation light beam 94. The excitation light beam 94 is coupled to the spectral analysis light path 36 for projecting on the fundus of the patient's eye 21 at the analysis spot. The excitation beam 94 may be absorbed by fluorescent compounds or the like present in the retina, exciting a singlet state of the fluorescent compounds. The excited compound will then thermally lose energy and emit light at the emission wavelength, which has a lower energy than the excitation photon. The emission being isotropic, a portion of the emitted light will be part of the return light 32 and take the imaging path 34, reach the beamsplitter 48, and go into the spectral analysis path 36. The presence of the longpass filter will block any reflected component at the excitation wavelength and let through the light at the emission wavelength.

The excitation light beam 94 may also be reflected by Raleigh scattering with no change in wavelength. The return light 32 from the fundus therefore further includes a reflected component 94' at the excitation wavelength, which propagates along the imaging light path 34 to the imaging device 50. Detecting the reflected component 94' of the excitation light beam using the imaging device 50 provides a visual representation of the analysis spot within the image of the fundus obtained in the illumination mode, as both the spectral analysis portion 56 of the return light 32 and the excitation light beam 94 follow a same optical path.

It will be readily understood that in some implementations, the excitation light beam may include more than one excitation wavelengths without departing from the scope of protection. By way of example, in coherent Raman spectroscopy applications, excitation of compounds in the medium may result from the coherent absorption of two photons at different wavelengths, and the excitation light beam 94 may therefore include photons at both these wavelengths. In other implementations, the excitation light beam may have a spectral profile within a spectral band or range including the desired excitation wavelength or wavelengths and excluding the emission wavelength or wavelengths.

It will be readily understood that the expression "analysis spot" refers to a region or area on the fundus of the patient's eye or other medium under analysis from which the portion of the return light reaching the spectral analyser originates. The analysis spot may have different sizes and/or shapes mostly determined by the optical design and configuration of the spectroreflectometric system.

Referring to FIGS. 5A to 5E and 6, examples of the results obtained through an implementation of the method and system described herein are shown. FIG. 6 shows a possible timing diagram for control signals provided to the spectral analyser 52, imaging device 50, illumination source 22 and excitation source 90. In accordance with some implementations, the spectroreflectometric system may include a controller 80 (shown in FIG. 1) generating the control signals and configured to operate in the illumination mode and in the excitation mode. In some implementations, the illumination mode and excitation modes may be operated alternatively, whereas in other implementations they may be operated concurrently. The control signals may have various profiles and it will be understood that the signals shown in FIG. 6 are provided for illustrative purposes only. For example, while the control signal for the imaging device is shown as an AC signal in FIG. 6, in other implementations a DC signal may be used.

Figure 5B:
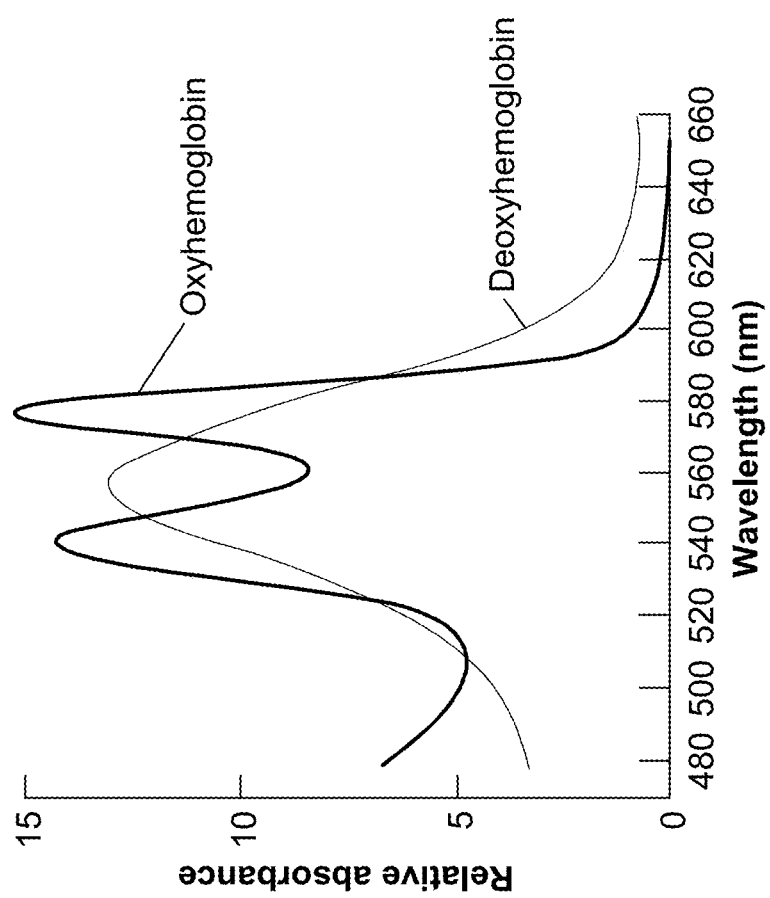
FIG. 5B shows a spectral analysis of an analysis spot on the fundus.
Figure 5A:
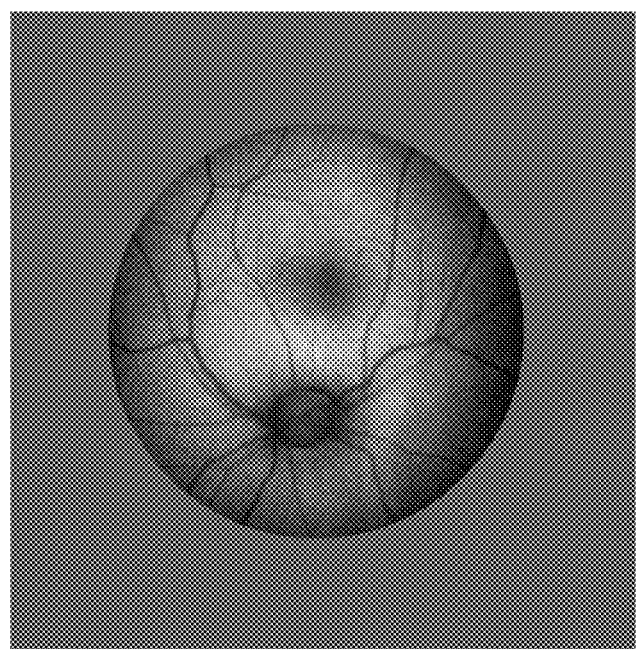
FIG. 5A shows an image of the fundus of a patient's eye acquired by the imaging device.

In the illumination mode $I_m$, the illumination source 22 and the imaging device 50 are turned on, whereas the excitation light source 90 is turned off. As a result, an image of the fundus of the eye is acquired by the imaging device, such as for example shown in FIG. 5A. Optionally the spectral analyser 52 may also be turned on in the illumination mode $I_m$, in which case a spectral analysis of the analysis spot can also be obtained, as shown in FIG. 5B. The spectral analysis is performed on the portion of the return light coupled to the spectral analysis path and reaching the spectral analyser. It is to be noted that the presence of the optical filter may remove spectral contents from the light reaching the spectral analyser, but that such a remove may not impact the results of the spectral analysis in cases where the optical filter is designed to block wavelengths outside of a spectral region of interest for such an analysis.

Figure 5E:
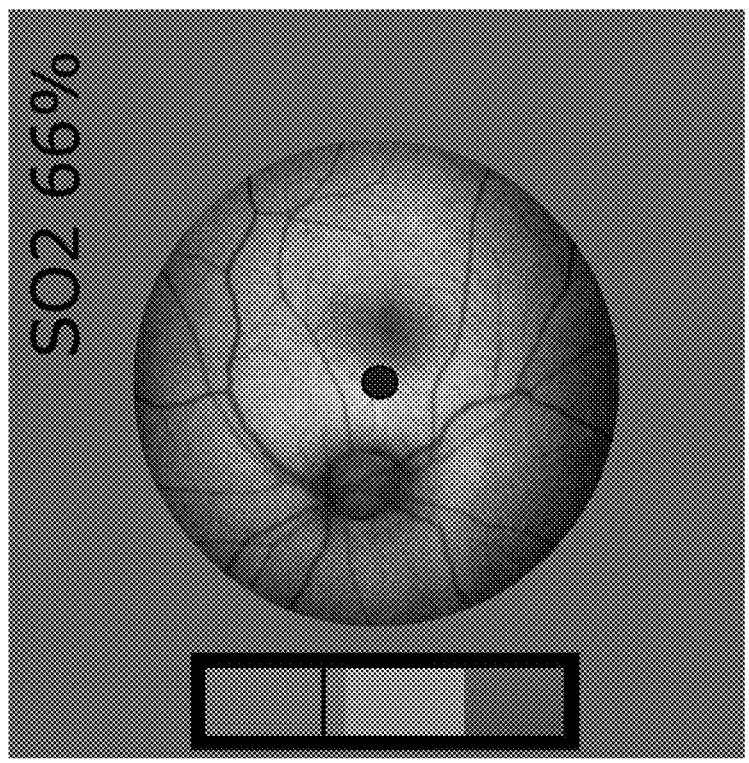
FIG. 5E shows the combined image of the fundus and the analysis spot thereon.

In the excitation mode $E_m$, the illumination source 22 is turned off, whereas the excitation light source 90 and spectral analyser 52 are turned on. The spectral analyser therefore receives light emitted following the excitation of a fluorescent compound in the fundus of the patient's eye. As mentioned above, reflected light at the excitation wavelength is blocked or substantially attenuated by the optical filter before reaching the spectral analyser. FIG. 5C shows an example of the light intensity vs wavelength information which can be obtained in this mode. This curve can be compared to the expected fluorescence from normative data to diagnose the potential presence of a pathology. The imaging device 50 may also be turned on in this mode, to collect an image of the analysis spot which will appear as a dot in the field of view of the imaging device, as shown in FIG. 5D. This image can be combined or otherwise associated with the image of the fundus obtained in the illumination mode, so that the position of the analysis spot on the fundus can be known and visualized, as seen in FIG. 5E. In this manner, the excitation light beam also acts as a pointer beam similar to a "laser pointer" pointing to the analysis spot from which the information on both graphs of FIGS. 5B and 5C originate.

In some implementations, it may be advantageous to operate the illumination light source in a continuous fashion. Such an operation may prevent the subject perceiving a flicker of light during the acquisition.

Figure 2:
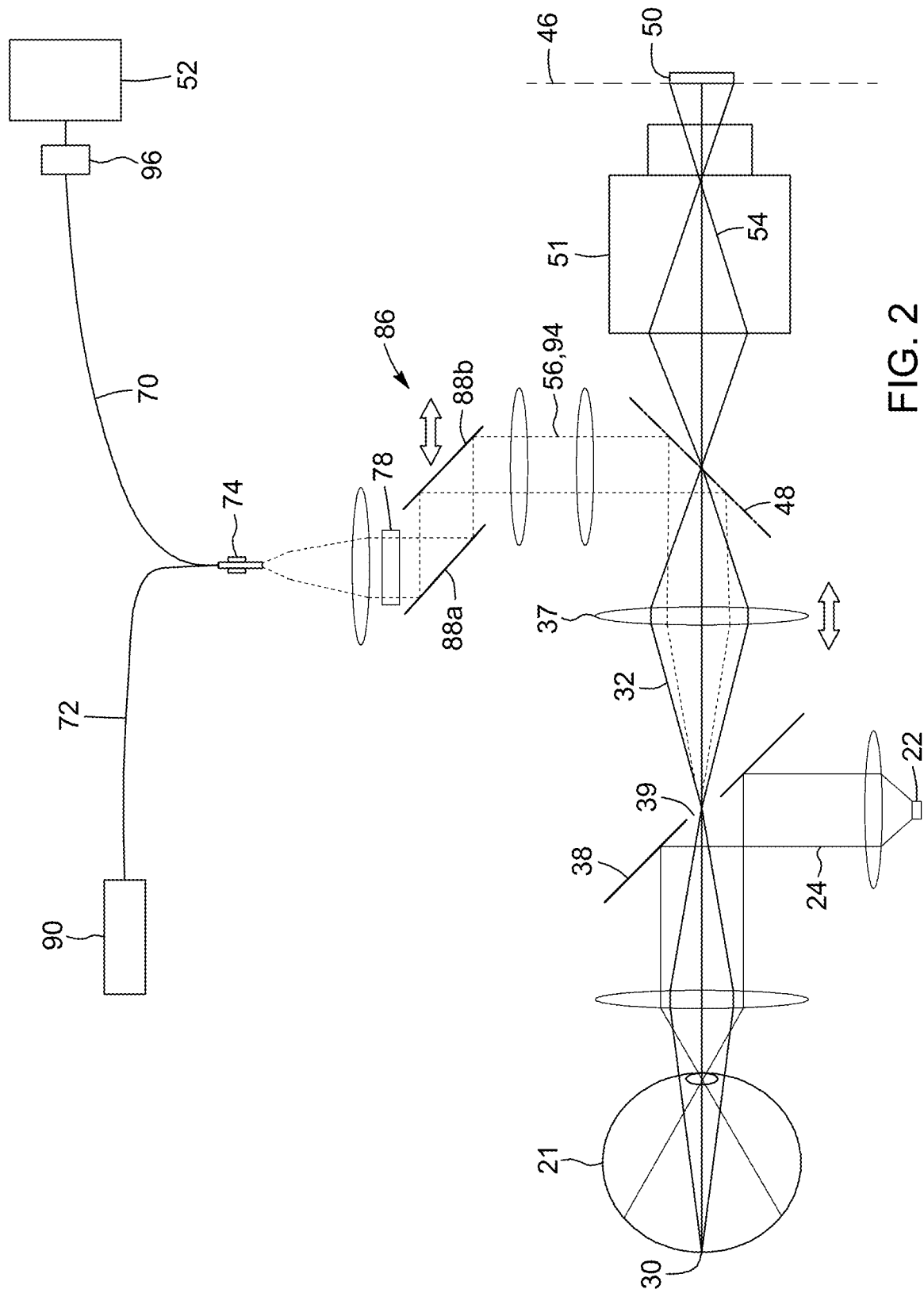
FIG. 2 is a detailed schematic representation of a system according to an embodiment.

Referring to FIG. 2, a schematized representation of a configuration embodying a spectroreflectometric system 20 according to one example is illustrated.

As mentioned above, the spectroreflectometric system 20 includes an imaging device 50. In some implementations, the imaging device 50 may be embodied by a CCD or CMOS sensor, or any surface that is sensitive and converts light intensity or energy into a useful signal. The imaging device 50 may include or be in communication with a processor, computer, circuit or any other hardware component or ensemble of hardware components programmed with instructions for constructing, storing and displaying the images acquired by the imaging device 50. An integrated or separate display may be provided to allow the viewing of the resulting images by an operator or user of the spectroreflectometric system 20.

The spectral analyser 52 may be embodied by any suitable device or combination of devices allowing an analysis of light as a function of wavelength. The spectral analyser 52 may for example be embodied by an optical spectrometer. As known to one skilled in the art, optical spectrometers decompose incoming light according to its wavelength, typically using light refraction (e.g. using a prism) or light diffraction (using a diffraction grating), and include a detector measuring the distributed intensity of the decomposed light. The spectral analyser 52 may include a computer or processor programmed with instructions to analyse the detected light spectrum in accordance with predetermined parameters, such as explained above. In some embodiments the spectral analyser 52 may be grating-based. It will however be readily understood that a variety of other configurations and structural components may be used without departing from the scope of the present description. By way of example, the spectral analyser 52 may include at least one dispersive element such as grating in reflection or transmission or a prism. In other implementations, the spectral analyser 52 may include a plurality of individual photodetectors each detecting a specific wavelength, for example using associated filters. In another example, the individual photodetectors may be spectrally separated by another dichroic/polarization/fiber circulator beam splitting arrangement, similar to the one used to separate the imaging and spectral analysis light paths.

The optical filter 96 may be embodied by any optical component having the desired transmissivity characteristics, such as a low light transmissivity at the excitation wavelength and a high light transmissivity at the emission wavelength. As mentioned above, the optical filter 96 may be a longpass filter, but in other variants the optical filter 96 may be a bandpass filter, a short-pass filter, a dynamic filter or the like. Referring to FIG. 3A, in one embodiment the optical filter 96 may for example include a pair of lenses, a first lens 98a coupled to the spectral analysis light path 36 that collimates the incoming light, and a second lens 98b that focuses the light into the spectral analyser 52. A optical filter 99, which possible embodiments have been described previously, is positioned between the two lenses. Referring to FIG. 3B, in another embodiment, the filtering medium is a really thin optical filter deposited directly at the output surface of an optical fiber 70 carrying light to the spectral analyser 52. In one embodiment, the filter is a hard coated optical filter. In another embodiment, the optical filter is a stack of absorbing materials, interference coatings and metallic layers laminated together. It will be readily understood that the configurations of FIGS. 3A and 3B are provided by way of example only and that other configurations providing the desired filtering effect may be envisioned.

The excitation light source 94 may be embodied by any light source generating a light beam 68 suitable for fluorescence generation or the triggering of other desired photoluminescent phenomena. In one example, the excitation light source 66 may be a laser diode. In other embodiment, the light source can be a LED with a specific filter that could be used via an optical fiber or simply at position 22. The excitation light beam 94 may have any wavelength or spectral contents safe for the eye of the patient (at least in ophthalmological applications) within the detection range of the imaging device and apt to generate fluorescence or other photoluminescent reaction from a compound present in the retina. The excitation light source may for example emit in the visible or near-infrared (NIR) spectral ranges. For example, lipofuscin present in A2E absorbs blue light, mostly between 450 and 480 nm. Melanin will be excited using a NIR source around 787 nm.

The spectroreflectometric system 20 may further include an illumination light source 22 operable to generate an illumination light 24, which can be projected towards the fundus 30 of the patient's eye 21 in the illumination mode. The illumination light source 22 may include one or more LED (Light Emitting Diode) emitters. The LED emitters of a given illumination light source 22 may have similar optical properties or different complementary optical properties selected in order to obtain, once combined, the desired optical properties for the illumination light 24. It will be readily understood that numerous other variants of light sources such as lasers, OLEDs, fluorescent, incandescent, tungsten, and other light bulbs may be used in alternative embodiments. The expression "illumination light" is used herein to refer to electromagnetic radiation suitable for projection into the eye 21 of a patient and for inducing, producing or otherwise generating return light 32 which can yield information of interest on the fundus 30 of the patient's eye 21 upon suitable analysis. It will be readily understood that the term "light" is not considered limited to the visible portion of the electromagnetic spectrum. The illumination light 24 preferably has a broadband spectral profile encompassing all the wavelengths of interest for the spectral analysis which the system is configured to perform. In some variants, the illumination light may be white light. In other variants, the illumination light 24 may have a spectral profile designed in view of the field of use of the spectroreflectometric system 20. In yet another set of variants, the illumination light may have any other suitable spectral profile as dictated by one or more factors such as the optical properties of the patient's eye, the availability of light sources, the nature and characteristics of the photoluminescence and/or spectral analysis to be performed, etc. By way of example, is some embodiments the illumination light may have a spectral profile selected to perform an autofluorescence imaging and/or mapping of the medium. This may for example be useful to locate fluorescent regions within the image of the medium, an select the analysis spot of the spectral analyser accordingly. In some variants, autofluorescent imaging may be accomplished by using a narrowband electromagnetic source such as a LED or laser emitting at the desired excitation wavelength as the illumination source, and providing a filter within the imaging light path (at any position between the beamsplitter 48 and the imaging device 50) which block this wavelength. In other variants, the illumination light source may combine broadband light with excitation light within a same beam, providing an autofluorescent map overlaid on the image of the medium. This may for example be accomplished by combining light beams from multiple sources using a dichroic filter.

As mentioned above, the spectroreflectometric system 20 may further include an optical assembly 26. The optical assembly 26 defines, on one hand, the imaging light path 34 between the patient's eye 21 and the imaging device 50 and, on the other hand, the spectral analysis light path 36 between the imaging light path 34, the patient's eye 21 and the spectral analyser 52.

It will be readily understood that the optical assembly 26 may be embodied by a variety of configurations suitable for the purpose of illuminating a patient's eye and collecting the resulting return light. The optical assembly 26 may include one or more optical components configured to transfer the image of the fundus 30 onto an image plane 46. The optical components may include lenses, mirrors, polarizers, filters, etc. The optical components may be arranged in any suitable fashion as is generally known to those skilled in the art. The optical assembly 26 may further include other non-optical components such as mechanical or electrical components providing structural and/or functional support to the optical components such as fixed or displaceable mounts, screens, pinholes, step motors, etc.

The optical assembly 26 may include an illumination subassembly 28 optically coupled to the illumination light source 22 and configured to project the illumination light 24 from the illumination light source 22 towards the fundus 30 of the patient's eye 21.

In the illustrated configuration, the illumination subassembly 28 includes a holed mirror 38 positioned at an angle along the imaging light path 34. The holed mirror 38 has a central hole 39 aligned with the imaging light path 34. Preferably, the illumination light source 22 is positioned orthogonally to the eye of the patient 21, and the holed mirror makes a 45° angle with respect to the optical axis of the illumination light 24. In alternative embodiments, the illumination subassembly 28 may include one or more optical components having variable transmission and reflection properties, for example a mirror designed to have a low reflectivity in the center and a high reflectivity around this center.

The illumination subassembly 28 may further include beam shaping optics projecting the illumination light 24 from the illumination light source 22 onto the holed mirror 38 for reflection towards the fundus of the patient's eye. The beam shaping optics may include one or more optical components interacting with the illumination light 24.

It will be readily understood that the illumination subassembly 28 may be embodied by any suitable collection of optical components and accompanying structural, mechanical, electrical or other features collaborating to bring the illumination light from the illumination light source to the patient's eye with the desired optical characteristics. The components of the illumination subassembly may redirect, focus, collimate, filter or otherwise act on light in a variety of fashions. One skilled in the art will readily understand that a multitude of designs may provide such a result. For example, in some variants, one or more optical fibers may be used to carry the illumination light 24 at least partially from the illumination light source 22 towards the fundus 30. It will be further understood that the illumination light source 22 may be provided either separately or integrally to the optical assembly 26. In one example, the optical assembly 26 may include a light port configured to receive the illumination light directly or indirectly from the illumination light source. It will be readily understood by one skilled in the art that numerous optical configurations may embody the illumination subassembly. By way of example, one such configuration is shown in international patent application no. PCT/CA2018/051559, the contents of which is incorporated herein by reference in its entirety.

Still referring to FIG. 2, the optical assembly 26 may further include the above-mentioned beamsplitter 48. The beamsplitter 48 is positioned along the imaging light path 34 and configured to allow a direct imaging portion 54 of the return light 32 travelling to the imaging light path 34, and divert a spectral analysis portion 56 of the return light 32 to the spectral analysis light path 36. It will be readily understood that, although in the illustrated variant the beamsplitter 48 is configured and arranged to transmit through the imaging portion 54 of the return light 32 and reflect the spectral analysis portion 56 of the return light 32, in other variants it may be configured and arranged to reflect the imaging portion 54 towards the imaging device 50, and transmit through the photoluminescence analysis portion 56 towards the spectral analyser 52.

In some implementations, a translatable focusing lens 37 may be positioned between the beamsplitter 48 and the imaging device 50. In some embodiments, the translatable focusing lens 37 may be mounted on a suitable translation actuator allowing its displacement along the imaging light path 34. Such a movement displaces the imaging plane 46 to compensate for refractive index variations in the eye of different patients. In other variants, the focusing lens 37 may have a variable focus and may be adjustable by different means.

The imaging portion 54 of the return light 32 travels along the imaging light path 34 until it reaches the imaging device 50 for detection. Of course, numerous optical components could be provided along the imaging light path to collimate, focus, filter, redirect or otherwise affect the imaging portion 54 prior to reaching the imaging device 50. Beam shaping optics 51 are indicated as a blackbox representation of such components in the illustrated configuration of FIG. 2.

The spectral analysis portion 56 of the return light 32 is deviated to the spectral analysis light path 36 and is eventually detected by the spectral analyser 54. The spectral analysis light path 36 is also optically coupled to the excitation light source 90 so that the excitation light beam 94 can counterpropagate along the spectral analysis light path 36 towards the beamsplitter 48. The operation of the excitation light source 66 and other features that may be provided along the spectral analysis light path 36 will be explained in further details below.

It will be readily understood that although in the illustrated variant the beamsplitter 48 is configured and arranged to transmit through the imaging portion 54 of the return light 32 and reflect the spectral analysis portion 56 of the return light 32, in other variants it may be configured and arranged to reflect the imaging portion 54 towards the imaging device 50, and transmit through the spectral analysis portion 56 towards the spectral analyser 52 according to polarisation directions.

The beamsplitter 48 may operate according to any one of various principles to separate the light impinging thereon according to different portions. In one embodiment, the beamsplitter 48 is a dichroic beamsplitter. As well known to those skilled in the art, dichroic optical components affect light according to their spectral characteristics. The dichroic beamsplitter 48 may have a spectral transmission profile tailored to the operation of the spectroreflectometric system 20.

In other embodiments, the beamsplitter 48 may separate light according to other characteristics than its spectral contents. The beamsplitter 48 may for example be configured to divide the return light 32 travelling along the imaging light path 34 into the imaging portion and the spectral analysis portion according to intensity ratios independently of the light's wavelength or polarization state. In other variants, the beamsplitter 48 may be configured to divide the return light 32 travelling along the imaging light path 34 into the imaging portion and the spectral analysis portion.

Referring still to FIG. 2, in some implementations, the optical assembly 26 includes first and second optical fiber links 70 and 72. The first optical fiber link 70 extends between the spectral analysis light path 34 and the spectral analyser 52. The second optical fiber link 72 extends between the spectral analysis light path 34 and the excitation light source 90. The optical assembly 26 further includes a three-prong coupler 74 optically coupling the spectral analysis light path 34, the first optical fiber link 70 and the second optical fiber link 72.

Figure 4C:
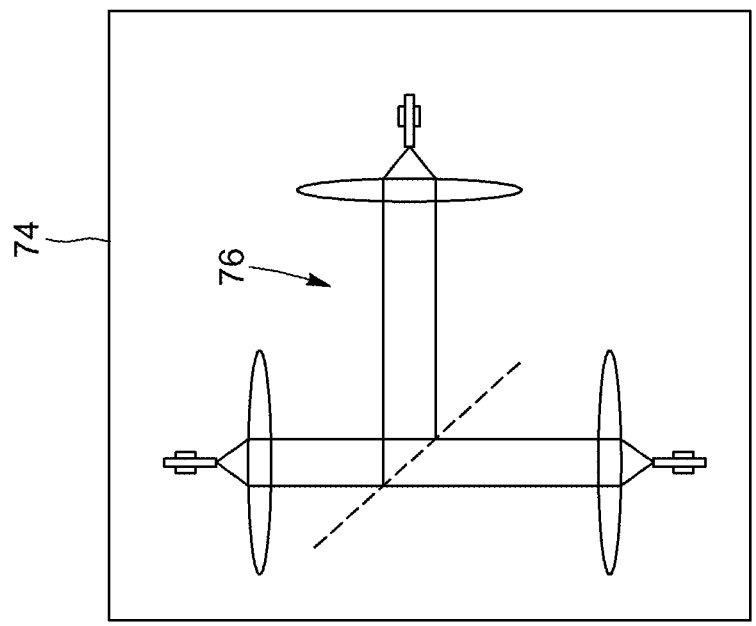
FIGS. 4A to 4C show different configurations of a three-prong coupler for use in a system according to some embodiments.
Figure 4B:
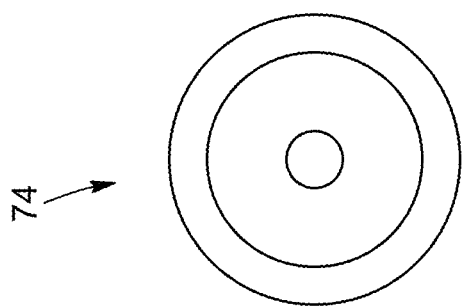
Figure 4A:
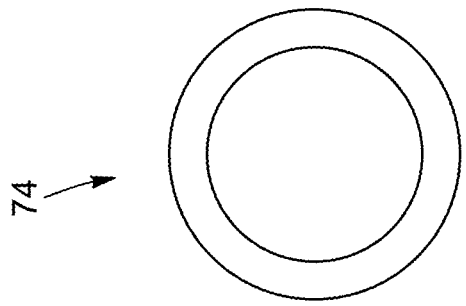

The three-prong coupler 74 may be embodied by various devices and/or configurations providing light circulation from the spectral analysis light path 36 to the first optical fiber link 70, allowing the spectral analysis portion 56 of the return light 32 to reach the spectral analyser 52, and from the second optical fiber link 72 to the spectral analysis path 36, allowing the excitation light beam 94 to be launched in the system towards the eye of the patient 21. Referring to FIGS. 4A to 4C, different variants of the three-prong coupler 74 are illustrated. In the example of FIG. 4A, the three-prong coupler 74 includes a multimode optical circulator. FIG. 4B shows another variant where the three-prong coupler 74 comprises a double-clad optical fiber, which may support the propagation of the pointer light beam in the core, and the light collection for spectral analysis region through the cladding sent to the spectral analyser. In this case, the core mode is optically coupled to the first optical fiber link, and the cladding mode is optically coupled to the second optical fiber link (or vice versa). In yet another variant, the three-prong coupler 74 may be a free-space configuration, for example based on a free-space beamsplitting configuration 76.

Of course, numerous optical components could be provided along the spectral analysis light path to collimate, focus, filter, redirect or otherwise affect the spectral analysis portion 56 prior to reaching the three-prong coupler 74. Beam shaping optics 78 are indicated as a blackbox representation of such components in the illustrated configuration of FIG. 2A. By way of example, a lens 79 focusing light onto the three-prong coupler 74 is also illustrated.

The spectroreflectometric system 20 may include additional components and functionalities.

Figure 7A:
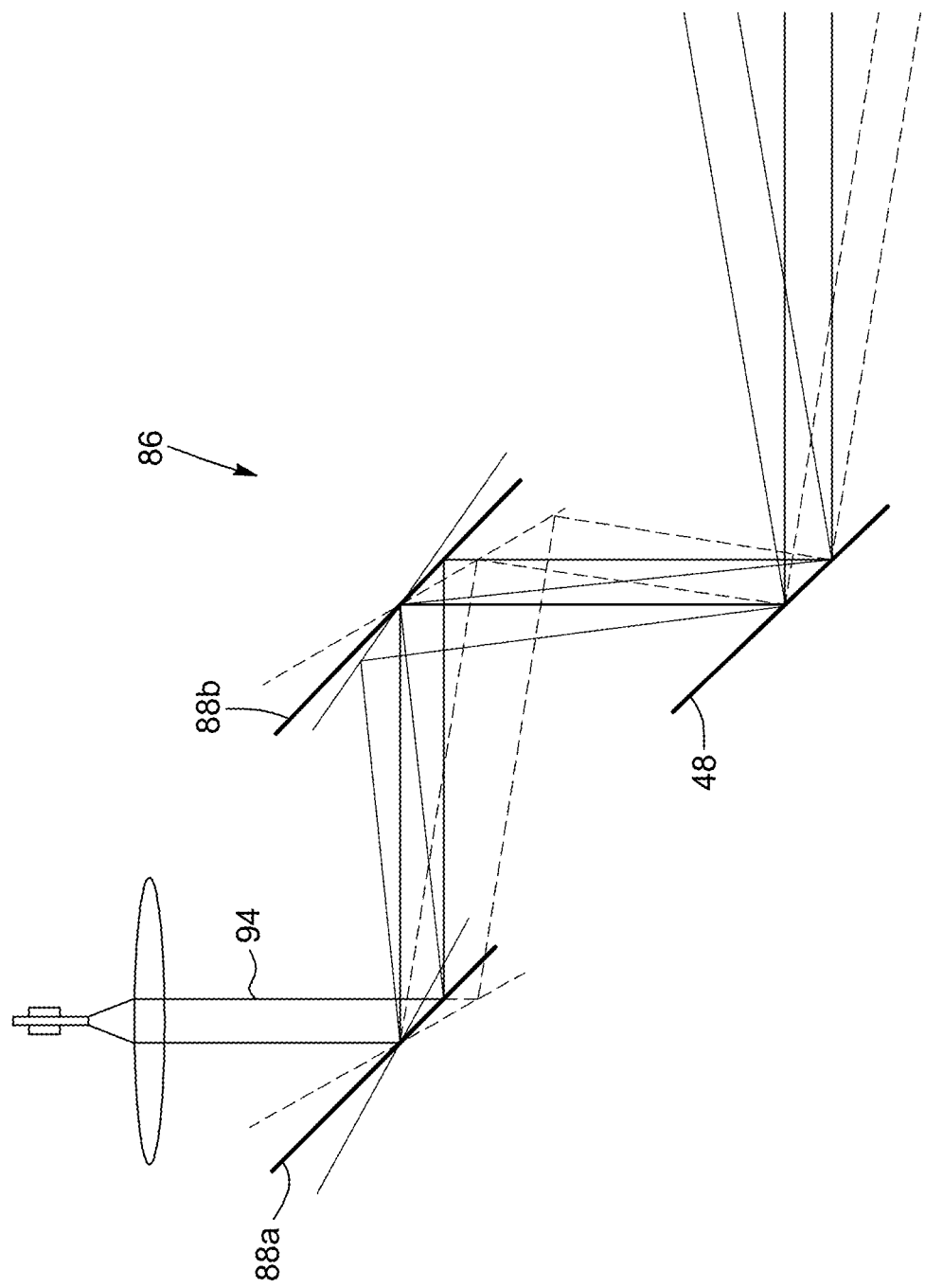
FIGS. 7A and 7B are examples of configuration for a spot shifting mechanism for use in a system according to one embodiment.
Figure 7B:
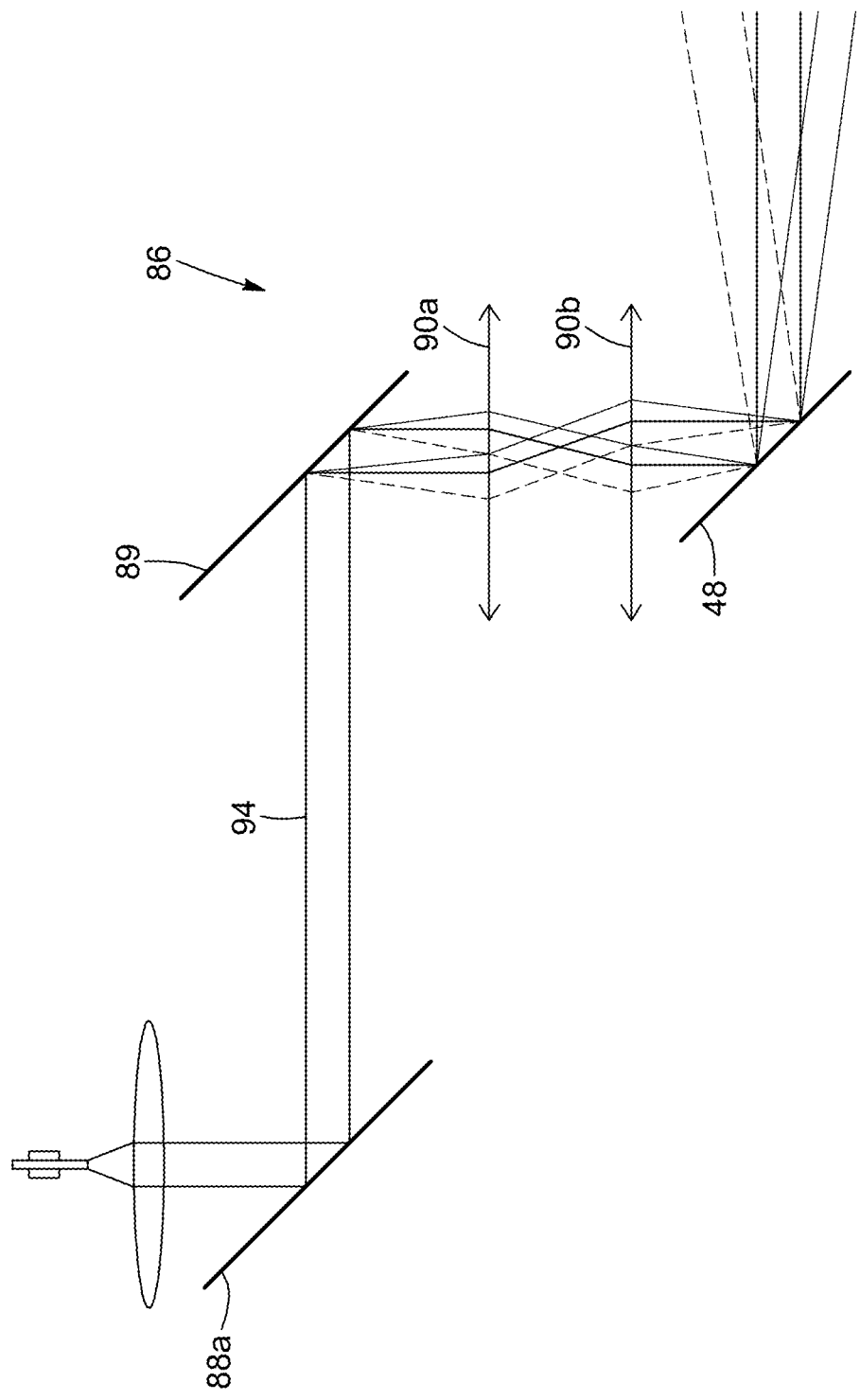

In some implementations, the spectroreflectometric system 20 may include a spot shifting mechanism 86 positioned in the spectral analysis path 36 and configured to shift the position of the analysis spot over the fundus 30 of the patient's eye without impact on the imaging portion 21. The spot shifting mechanism 86 may include shift optics such as one or more steerable mirrors. A pivoting of the steerable mirrors can be used to change the incidence angle between the excitation light beam 94 travelling along the spectral imaging light path 36 and the beamsplitter 48. Referring to FIGS. 7A and 7B, two examples of configurations of the spot shifting mechanism are shown. On FIG. 7A, the first and second mirrors 88a, 88b with displacement both in phi and theta directions are used to change the angle of incidence of the excitation light beam 94 onto the beamsplitter 48. The direction of displacement of the first mirror 88a is opposite to one of the second mirror 88b in order to keep the position of the excitation light beam 94 on the beamsplitter 48 and to only change the angle of incidence. In FIG. 7B, a gimbal mirror 89 is used in place of the second mirror 88b. This scheme, used jointly with two lenses 90a and 90b used in a 4f configuration, enables the variation of the angle of incidence of the excitation light beam 94 onto the beamsplitter 48 without changing the position at which the excitation light beam 94 hits the beamsplitter.

In some variants, a spectroreflectometric system 20 similar to the one described above may be used in performing a spectral analysis on a medium other than the fundus of the eye. By way of example, in some implementations the medium under study may be a pouch of liquid, for example containing blood or plasma. In such a variant the spectroreflectometric system may for example include all the same components as the system shown in FIG. 2, including the optical assembly 26 and illumination subassembly 28. In this variant, the illumination subassembly 28 may further include an additional output lens. The additional output lens can be added to the configuration of FIG. 2 to provide focalization and form an image of the medium being probed on the imaging device 50. As one skilled in the art will readily understand, this approach can provide an easy adaptation of a system initially conceived to probe the fundus of the eye 21, since such a conception considers the natural light focalisation performed by the lens of the eye, which is in essence replaced by the additional output lens. In other variants, the output lens and additional output lens may be replaced by a single lens or different optical arrangement.

In accordance with another aspect, there is provided a method for performing a photoluminescence analysis on a medium.

In some implementations of the method, the medium may be the fundus of a patient's eye, as explained above. In other implementations, the medium may be other than the eye such as for example the skin, organ tissues, exposed muscle tissues, and other biological tissues or fluids. In some embodiments the medium under study may be an ex-vivo sample such as blood, tissues, etc. stored in a transparent container such as a bag, a vial, a syringe or a cuvette, or on a suitable substrate.

The method first includes providing an imaging device, a spectral analyser, an optical assembly defining an imaging light path between the medium and the imaging device and a spectral analysis light path between an analysis spot on the medium and the spectral analyser, an excitation light source optically coupled to the spectral analysis path and operable to generate an excitation light beam comprising an excitation wavelength selected to excite components present in the medium for the generation of photoluminescent light at an emission wavelength differing from the excitation wavelength, and an optical filter coupled to the spectral analyser, the optical filter having a low light transmissivity at the excitation wavelength and a high light transmissivity at the emission wavelength, and an illumination light source. Of course, it will be readily understood that systems such as those described above may be used.

The method further includes operating the illumination light source to project illumination light towards the medium, and operating the imaging device to obtain an image of the medium. Optionally, the excitation light source may be operated with the imaging device to further to obtain an image of the analysis spot. The image of the analysis spot may be superimposed on the image of the medium, as shown in FIG. 5E. In this manner, an operator may for example visualize from which region of the fundus the photoluminescence analysis is obtained.

The method further includes operating the excitation light source to project the excitation light beam on said analysis spot and the spectral analyser to obtain a photoluminescence measurement of the analysis spot on said fundus. The photoluminescence measurement may be one of an absorbance measurement, a fluorescence measurement, an autofluorescence measurement, a spontaneous Raman spectroscopy measurement and coherent Raman spectroscopy measurement.

The photoluminescence measurement may then be used to provide an analysis of one or more parameters from the medium. As explained above, such data may be used, for example, to quantify lipofuscin granules in the fundus of the patient's eye.

Of course, numerous modifications could be made to the embodiments described above without departing from the scope of the invention as described in the appended claims.

The invention claimed is:

1. A system for performing a photoluminescence analysis on a medium, comprising:
   an illumination subassembly configured to project illumination light towards the medium and an illumination light source operable to generate the illumination light and optically coupled to the illumination subassembly;
   an imaging device configured to acquire an image of the medium including an analysis spot;
   an excitation light source operable to generate an excitation light beam comprising an excitation wavelength selected to excite components present in the medium for the generation of photoluminescent light at an emission wavelength differing from the excitation wavelength;
   a spectral analyser;
   an optical assembly defining an imaging light path between the medium and the imaging device and a spectral analysis light path between the analysis spot on the medium and the spectral analyser,
   the excitation light source being optically coupled to the spectral analysis light path for projecting the excitation light beam on said analysis spot, the spectral analyser being configured to analyse return light from the analysis spot as a function of wavelength; and
   an optical filter coupled to the spectral analyser, the optical filter having a low light transmissivity at the excitation wavelength and a high light transmissivity at the emission wavelength.

2. The system according to claim 1, comprising a beamsplitter positioned and configured to direct an imaging portion of return light from the medium travelling along the imaging light path to the imaging device and a spectral analysis portion of said return light to the spectral analysis light path.

3. The system according to claim 2, wherein the beamsplitter is a dichroic beamsplitter.

4. The system according to claim 3, wherein the beamsplitter is configured to divide the light travelling along the imaging light path into the imaging portion and the spectral analysis portion according to one of intensity ratios and polarisation directions.

5. The system according to claim 1, comprising:
   a) a first optical fiber link extending between the spectral analysis light path and the spectral analyser;
   b) a second optical fiber link extending between the spectral analysis light path and the excitation light source; and
   c) a three-prong coupler optically coupling the spectral analysis light path, the first optical fiber link and the second optical fiber link.

6. The system according to claim 5, wherein the three-prong coupler comprises one of a multimode optical circulator, a double-clad optical fiber and a free-space beamsplitting configuration.

7. The system according to claim 5, wherein the optical filter comprises a free-space optical component disposed between the first optical fiber link and the spectral analyser.

8. The system according to claim 5, wherein the optical filter comprises a thin film deposited on a fiber-based component disposed between the first optical fiber link and the spectral analyser.

9. The system according to claim 1, wherein the optical filter is a longpass optical filter or a bandpass optical filter.

10. The system according to claim 1, further comprising a controller generating control signals for controlling the illumination light source, the imaging device, the spectral analyser and the excitation light source.

11. The system according to claim 1, wherein the controller is configured to operate in:
   an illumination mode wherein the controller turns on at least the illumination device and the imaging device; and
   an excitation mode wherein the controller turns on at least the excitation light source and the spectral analyser.

12. The system according to claim 1, further comprising a controller configured to operate in:
   an illumination mode wherein the controller operates the illumination device to project said illumination light towards the medium, the imaging device to obtain an image of the medium and the spectral analyser to obtain a spectral analysis of the analysis spot on medium; and
   an excitation mode wherein the controller operates the excitation light source to project the excitation light beam on said analysis spot and the spectral analyser to obtain a photoluminescence analysis of the analysis spot on said medium.

13. The system according to claim 1, further comprising a spot shifting mechanism positioned in the spectral analysis light path and configured to shift a position of the analysis spot over said medium.

14. A method for performing a photoluminescence analysis on a medium, comprising:
   a) providing an imaging device, a spectral analyser, an optical assembly defining an imaging light path between the medium and the imaging device and a spectral analysis light path between an analysis spot on the medium and the spectral analyser, an excitation light source optically coupled to the spectral analysis path and operable to generate an excitation light beam comprising an excitation wavelength selected to excite components present in the medium for the generation of photoluminescent light at an emission wavelength differing from the excitation wavelength, and an optical filter coupled to the spectral analyser, the optical filter having a low light transmissivity at the excitation wavelength and a high light transmissivity at the emission wavelength, and an illumination light source;
   b) operating the illumination light source to project illumination light towards the medium, and operating the imaging device to obtain an image of the medium; and c) operating the excitation light source to project the excitation light beam on said analysis spot and the spectral analyser to obtain a photoluminescence measurement of the analysis spot on said fundus.

15. The method according to claim 14, further comprising operating the excitation light source and the imaging device to obtain an image of said analysis spot.

16. The method according to claim 15, further comprising a step of superimposing the image of the analysis spot on the image of the medium.

17. The method according to claim 14, wherein the medium is the fundus of a patient's eye.

18. The method according to claim 14, wherein said photoluminescence measurement comprises one of an absorbance measurement, a fluorescence measurement, an autofluorescence measurement, a spontaneous Raman spectroscopy measurement and coherent Raman spectroscopy measurement.

* * * * *